United States Patent
Lan et al.

(10) Patent No.: US 8,512,266 B2
(45) Date of Patent: Aug. 20, 2013

(54) ORTHOPEDIC ADJUSTMENT DEVICE

(75) Inventors: Hai Lan, Taipei Hsien (TW); Ga-Lane Chen, Santa Clara, CA (US); Yu-Bin Wang, Taipei Hsien (TW)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 246 days.

(21) Appl. No.: 12/958,564

(22) Filed: Dec. 2, 2010

(65) Prior Publication Data

US 2011/0301519 A1    Dec. 8, 2011

(30) Foreign Application Priority Data

Jun. 3, 2010  (TW) .................................. 99117964 A

(51) Int. Cl.
*A61F 5/00* (2006.01)
(52) U.S. Cl.
USPC .................... 602/13; 602/5; 602/19; 601/148
(58) Field of Classification Search
USPC ............... 602/13, 19, 5; 604/9, 67, 181, 189, 604/235, 892.1; 601/43–44, 148–152
See application file for complete search history.

(56) References Cited

U.S. PATENT DOCUMENTS

| | | | | |
|---|---|---|---|---|
| 5,733,256 A * | 3/1998 | Costin | ............................. | 604/22 |
| 5,827,209 A * | 10/1998 | Gross | .............................. | 602/19 |
| 5,950,628 A * | 9/1999 | Dunfee | ......................... | 128/874 |
| 6,540,707 B1 * | 4/2003 | Stark et al. | ....................... | 602/13 |
| 6,905,456 B1 * | 6/2005 | Brunner et al. | ................. | 600/16 |

* cited by examiner

*Primary Examiner* — Patricia Bianco
*Assistant Examiner* — Camtu Nguyen
(74) *Attorney, Agent, or Firm* — Altis Law Group, Inc.

(57) ABSTRACT

An exemplary orthopedic adjustment device includes an orthopedic appliance, an adjustment unit module and a pressure control module. The appliance is configured for supporting a human spine. The adjustment unit module includes adjustment units. Each of the adjustment units includes a chamber, a pressure sensor and a pump. The pressure sensor and the pump are arranged in the chamber. Each of the pressure sensors is configured for detecting a pressure of each chamber corresponding thereto. Each of the pumps is configured for adjusting the pressure of each chamber corresponding thereto. The pressure control module is configured for receiving pressure signals from the pressure sensors of the chambers and providing pressure adjusting signals to the pumps to adjust the pressures of the chambers.

8 Claims, 5 Drawing Sheets

ORTHOPEDIC ADJUSTMENT DEVICE

CROSS-REFERENCE TO RELATED APPLICATION

This application is based upon and claims the benefit of priority from Taiwanese Patent Application No. 99117964, filed Jun. 3, 2010, the entire contents of which are incorporated herein by reference.

BACKGROUND

1. Technical Field

The disclosure relates generally to orthopedic treatment of patients, and more particularly to an orthopedic adjustment device with pressure sensors.

2. Description of the Related Art

Scoliosis or other orthopedic conditions can be treated by an orthopedic appliance. However, most such orthopedic appliances are uncomfortable to wear. Moreover, correction or adjustment of a conventional orthopedic appliance must be performed manually.

Thus, what is called for is an orthopedic adjustment device that can overcome the limitations described.

DETAILED DESCRIPTION

Figure 1:
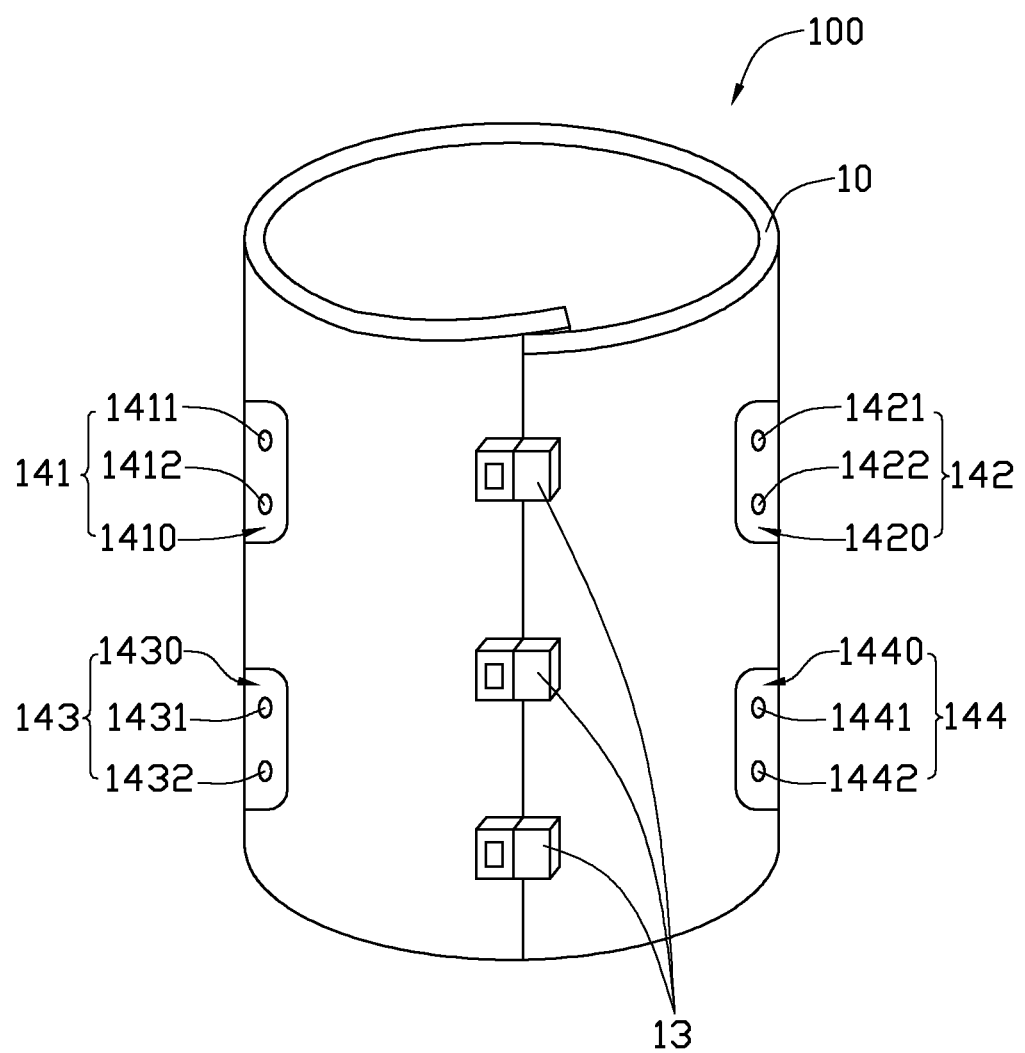
FIG. 1 is an isometric view of an orthopedic adjustment device in accordance with one embodiment of the disclosure, showing the orthopedic adjustment device in a fastened state ready for use.
Figure 2:
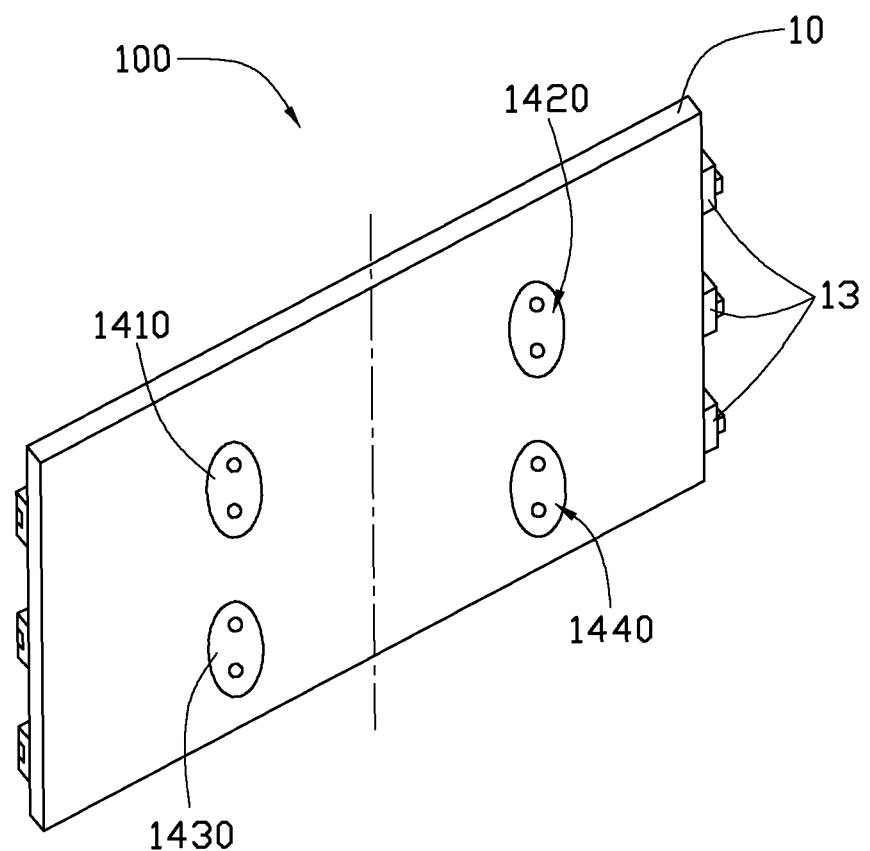
FIG. 2 is a view of the orthopedic adjustment device of FIG. 1, but showing the orthopedic adjustment device in an unfastened state.
Figure 3:
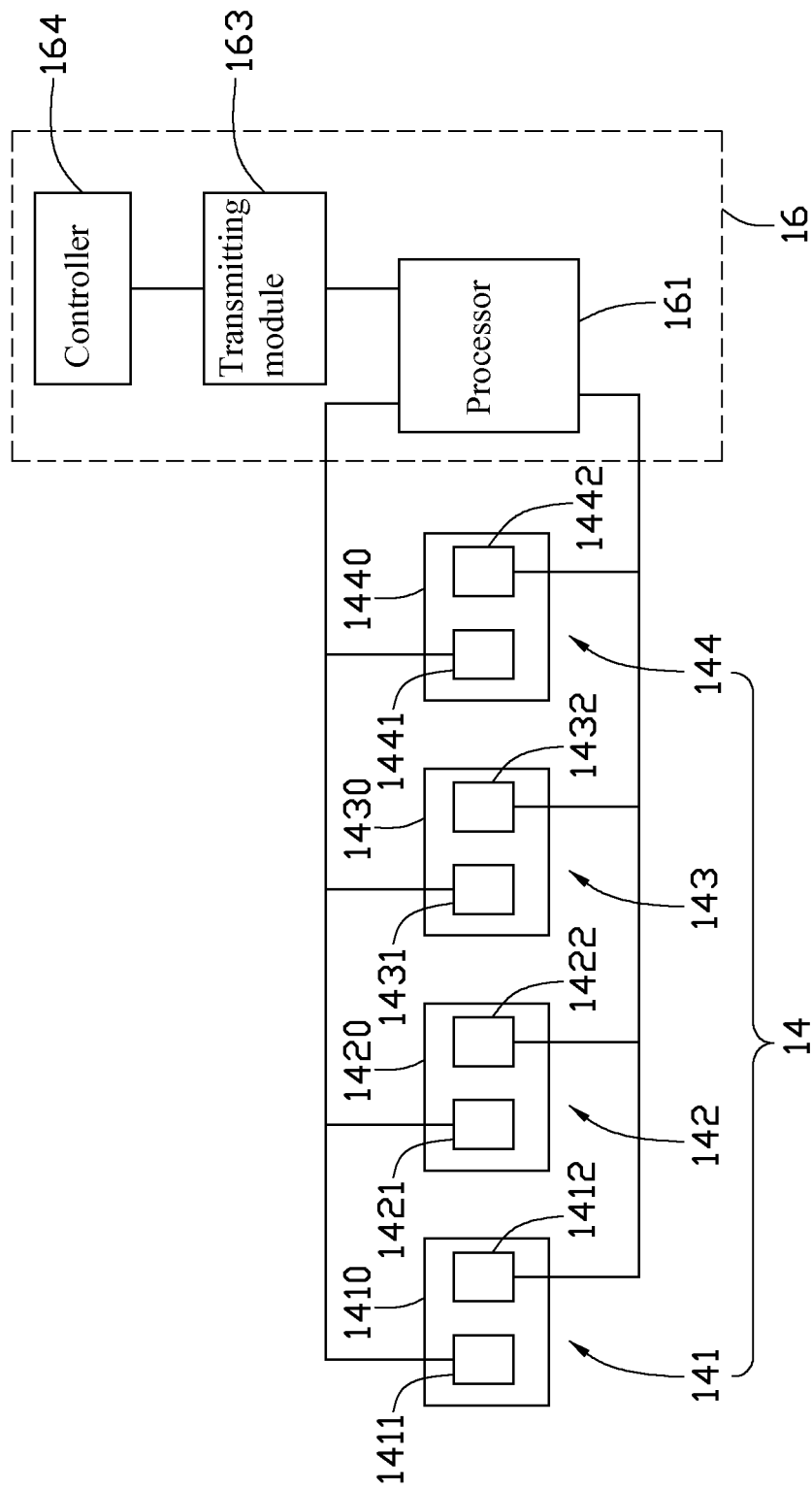
FIG. 3 is a block diagram of main components of the orthopedic adjustment device of FIG. 1.

Referring to FIGS. 1-3, an orthopedic adjustment device 100 in accordance with one embodiment of the disclosure includes an orthopedic appliance 10, a plurality of fasteners 13, an adjustment unit module 14 and a pressure control module 16.

Figure 4:
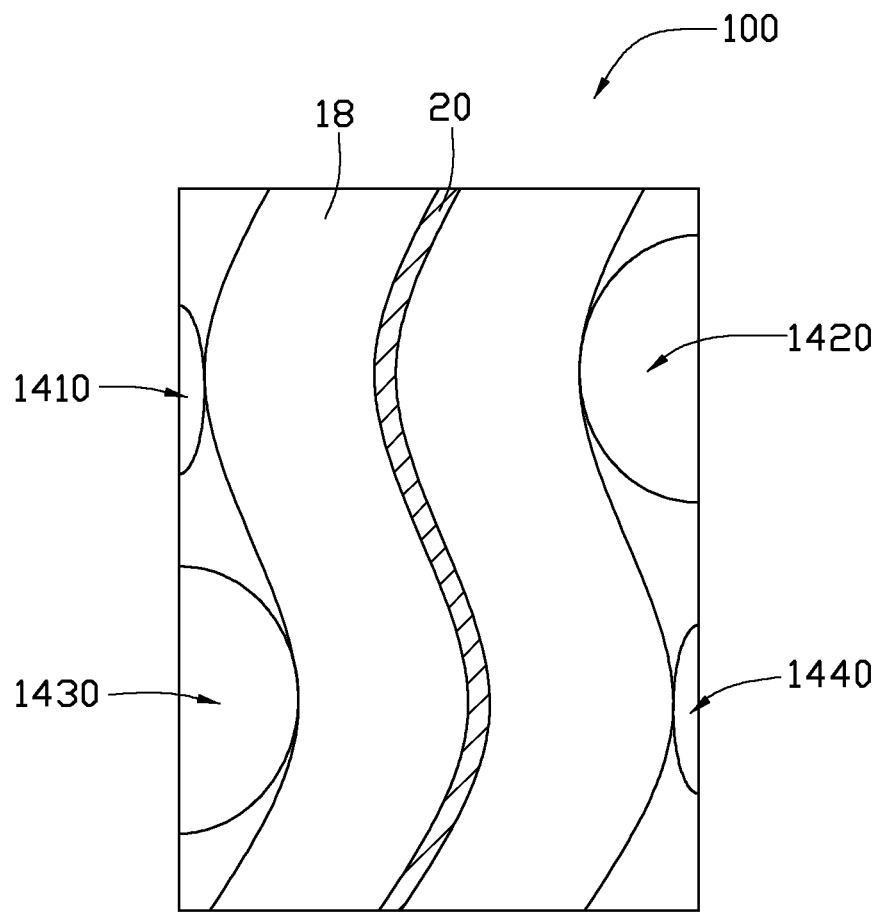
FIG. 4 is a schematic, cross-sectional view of the orthopedic adjustment device of FIG. 1 worn around the trunk of a patient, showing chambers of the orthopedic adjustment device before pressures of the chambers have been adjusted.

Referring also to FIG. 4, the appliance 10 is worn around the torso of a human patient 18, and is configured for supporting the spine of the patient 18. The appliance 10 is typically made of plastic. Fasteners 13 are arranged on and configured for fastening the appliance 10 in position around the torso of the patient 18.

The adjustment unit module 14 is for adjusting pressure applied by the orthopedic adjustment device 100 to various parts of the torso of the patient 18. In one embodiment, the adjustment unit module 14 includes a first adjustment unit 141, a second adjustment unit 142, a third adjustment unit 143 and a fourth adjustment unit 144. The adjustment units 141, 142, 143, 144 are arranged on the inner surface of the appliance 10. The adjustment units 141, 142, 143, 144 are provided at locations corresponding to lateral sides of the torso of the patient 18 when the orthopedic appliance 100 is worn around the torso of the patient 18.

The first adjustment unit 141 includes a first chamber 1410, a first pressure sensor 1411 and a first pump 1412. The second adjustment unit 142 includes a second chamber 1420, a second pressure sensor 1421 and a second pump 1422. The third adjustment unit 143 includes a third chamber 1430, a third pressure sensor 1431 and a third pump 1432. The fourth adjustment unit 144 includes a fourth chamber 1440, a fourth pressure sensor 1441 and a fourth pump 1442. The chambers 1410, 1420, 1430, 1440 can be air chambers or liquid chambers. The pumps 1412, 1422, 1432, 1442 can be air (pneumatic) pumps, liquid (hydraulic) pumps, magnetic pumps or electromagnetic pumps. In the present embodiment, the chambers 1410, 1420, 1430, 1440 are air chambers, and the pumps 1412, 1422, 1432, 1442 are air pumps. The number of chambers, pressure sensors and pumps can be determined according to specific needs, there being no limitation to the number of chambers, pressure sensors and pumps as disclosed.

The pressure sensors 1411, 1421, 1431, 1441 and the pumps 1412, 1422, 1432, 1442 are arranged in the chambers 1410, 1420, 1430, 1440.

The chambers 1410, 1420, 1430, 1440 are made of rubber. The pressure sensors 1411, 1421, 1431, 1441 are micro-electromechanical system (MEMS) pressure sensors, such as piezo-resistive micro-pressure sensors. The pumps 1412, 1422, 1432, 1442 are micro-electromechanical system (MEMS) pumps, such as piezoelectric micro-pumps.

Each of the pressure sensors 1411, 1421, 1431, 1441 is configured for detecting a pressure of each chamber 1410, 1420, 1430, 1440, respectively. Each of the pumps 1412, 1422, 1432, 1442 is configured for adjusting the pressure of each chamber 1410, 1420, 1430, 1440, respectively.

The pressure control module 16 includes a processor 161, a transmitting module 163 and a controller 164. The pressure control module 16 is electrically connected to the adjustment unit module 14.

The processor 161 is configured for receiving pressure signals from the pressure sensors 1411, 1421, 1431, 1441. The processor 161 provides scoliosis data to the controller 164 according to the pressure signals from the pressure sensors 1411, 1421, 1431, 1441 and normal (reference) configuration data stored in the processor 161 and the controller 164.

The controller 164 further includes a display device (not shown). The scoliosis data can be shown on the display device. The controller 164 is configured for providing orthopedic adjustment data to the processor 161 according to the scoliosis data and the normal configuration data. The transmitting module 163 is configured for transmitting the scoliosis data and orthopedic adjustment data between the processor 161 and the controller 164. The transmitting module 163 can be a Bluetooth module. (Bluetooth is a registered certification mark.)

The processor 161 is configured for providing pressure adjusting signals to the pumps 1412, 1422, 1432, 1442 according to the orthopedic adjustment data. Each of the pumps 1412, 1422, 1432, 1442 is configured for adjusting the pressure of each chamber 1410, 1420, 1430, 1440, respectively, according to the pressure adjusting signals. The processor 161 can be a microcontroller unit (MCU).

Referring to FIG. 4, the patient 18 and a spine 20 of the patient 18 are generally S-shaped. The chambers 1410, 1420, 1430, 1440 experience different pressures from the patient 18. Thus, the pressure sensors 1411, 1421, 1431, 1441 provide pressure signals to the processor 161 according to the pressures of the chambers 1410, 1420, 1430, 1440. The processor 161 provides scoliosis data to the controller 164 according to the pressure signals and the normal configuration data.

The controller 164 provides the orthopedic adjustment data to the processor 161 according to the scoliosis data and the normal configuration data. The processor 161 provides the pressure adjusting signals to the pumps 1411, 1421, 1431, 1441 of the chambers 1410, 1420, 1430, 1440 according to the orthopedic adjustment data.

Figure 5:
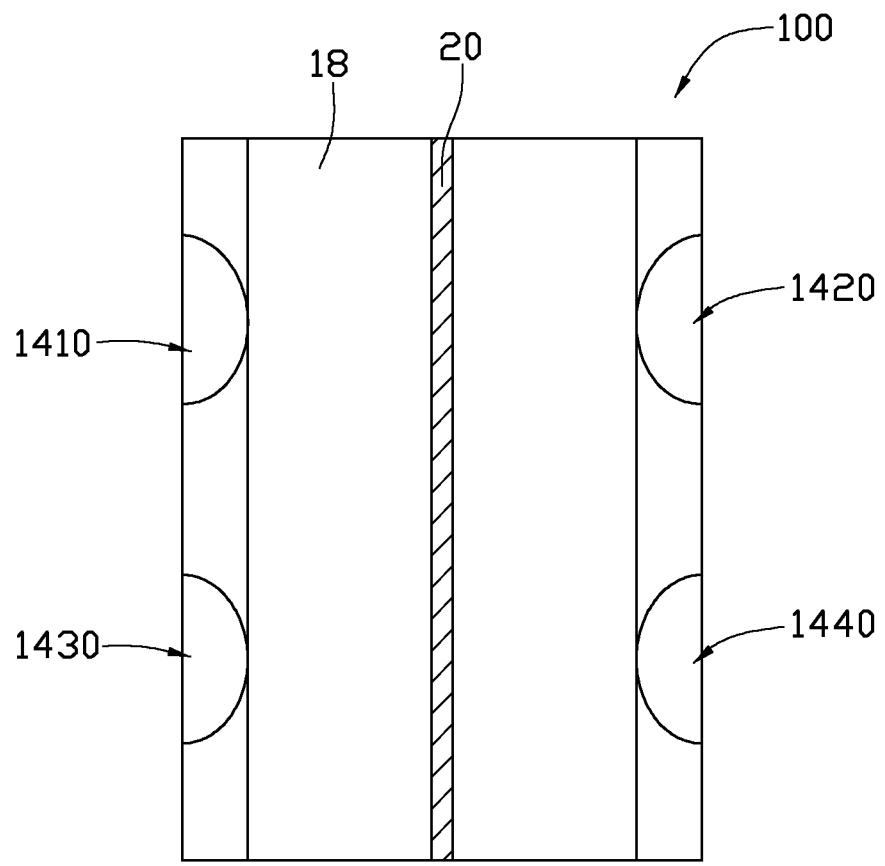
FIG. 5 is similar to FIG. 4, but showing the trunk of the patient after the pressures of the chambers have been adjusted.

Referring to FIG. 5, each of the pumps 1411, 1421, 1431, 1441 adjusts the pressure of each of the chambers 1410, 1420, 1430, 1440, respectively, according to the pressure adjusting signals from the processor 161. When the pressures of the chambers 1410, 1420, 1430, 1440 are adjusted, the curvature 20 can be alleviated or corrected by the orthopedic adjustment device 100. If necessary, the above-described processes can be repeated iteratively until the pressures of the chambers 1410, 1420, 1430, 1440 are adjusted satisfactorily.

While the above has been described by way of example and in terms of exemplary embodiments, it is to be understood that the disclosure is not limited thereto. To the contrary, the disclosure is intended to cover various modifications and similar arrangements, as would be apparent to those skilled in the art. Therefore, the scope of the appended claims should be accorded the broadest interpretation so as to encompass all such modifications and similar arrangements.

What is claimed is:

1. An orthopedic adjustment device comprising:
   an orthopedic appliance configured for supporting a human spine;
   an adjustment unit module comprising a plurality of adjustment units, the adjustment units provided at an inner surface of the orthopedic appliance, at locations on the orthopedic appliance corresponding to lateral sides of a human torso when the orthopedic appliance is worn around the torso, each of the adjustment units comprising a chamber, a pressure sensor and a pump, the pressure sensor and the pump arranged in the chamber, the pressure sensor configured for detecting a pressure of the chamber, the pump configured for adjusting the pressure of the chamber; and
   a pressure control module electrically connected to the adjustment unit module, the pressure control module configured for receiving pressure signals from the pressure sensors and providing pressure adjusting signals to the pumps to adjust the pressures of the chambers.

2. The orthopedic adjustment device of claim 1, wherein the pump is selected from the group consisting of an air pump, a liquid pump, a magnetic pump and an electromagnetic pump.

3. The orthopedic adjustment device of claim 1, wherein the chamber is selected from the group consisting of an air chamber and a liquid chamber.

4. The orthopedic adjustment device of claim 1, wherein the pressure sensor is a micro-electromechanical system pressure sensor.

5. The orthopedic adjustment device of claim 1, wherein the pump is a micro-electromechanical system pump.

6. The orthopedic adjustment device of claim 1, wherein the orthopedic appliance is made of plastic.

7. The orthopedic adjustment device of claim 1, further comprising a plurality of fasteners configured for fastening the orthopedic appliance in position around the torso.

8. The orthopedic adjustment device of claim 1, wherein the chamber is made of rubber.

\* \* \* \* \*